United States Patent [19]
Mikulicz

[11] 3,931,352
[45] Jan. 6, 1976

[54] HF ACID TREATING THE PARAFFIN FEED STREAM TO AN INTEGRATED PARAFFIN ISOMERIZATION-ALKYLATION PROCESS

[75] Inventor: Michael Z. Mikulicz, Palatine, Ill.
[73] Assignee: Universal Oil Products Company, Des Plaines, Ill.
[22] Filed: July 11, 1974
[21] Appl. No.: 487,514

[52] U.S. Cl. ...... 260/683.49; 260/683.65; 208/223; 208/254 R
[51] Int. Cl.² ...................... C07C 3/54; C07C 5/24
[58] Field of Search..... 260/683.49, 683.65, 683.68, 260/683.48, 683.4 R

[56] References Cited
UNITED STATES PATENTS
3,254,137 5/1966 Hutto et al..................... 260/683.48
3,650,943 3/1972 Schuller...................... 260/683.4 R
3,830,871 8/1974 Mayer et al................... 260/683.68

Primary Examiner—Delbert E. Gantz
Assistant Examiner—G. J. Crasanakis
Attorney, Agent, or Firm—James R. Hoatson, Jr.; Robert W. Erickson; William H. Page, II

[57] ABSTRACT

The normal paraffin feed stream to an integrated paraffin isomerization-HF acid-catalyzed alkylation process is treated for the removal of catalyst deactivating sulfur and nitrogen compounds and water by contacting the feed stream with liquid hydrofluoric acid. The treated feed stream is separated from the acid by gravity settling, charged to an alkylate fractionator, and passed through the isomerization process to form an isomerate which is returned to the alkylate fractionator and becomes a feed stream to the alkylation zone.

12 Claims, 1 Drawing Figure

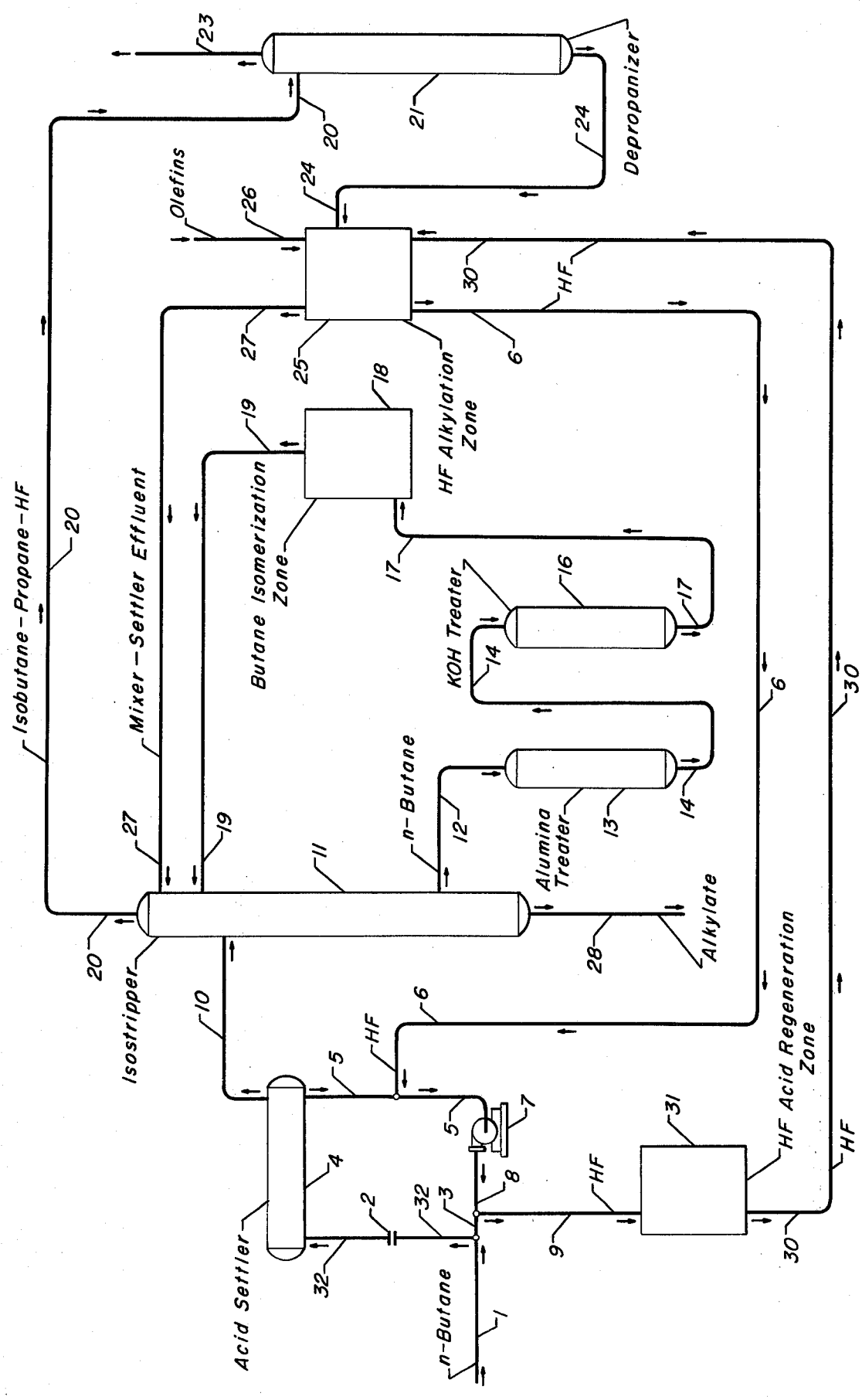

HF ACID TREATING THE PARAFFIN FEED STREAM TO AN INTEGRATED PARAFFIN ISOMERIZATION-ALKYLATION PROCESS

BACKGROUND OF THE INVENTION

1. Field of the Invention

The invention pertains to the treatment of a hydrocarbon stream by contacting it with hydrofluoric acid. It is specifically directed to a normal paraffin isomerization process wherein the feed stream is contacted with liquid hydrofluoric acid to thereby remove isomerization catalyst deactivating substances from the feed stream. The invention also relates to an integrated HF alkylation-isomerization process wherein the isomerate produced in the isomerization zone is fractionated in the isostripper and then reacted with a mono-olefin.

2. Description of the Prior Art

As indicated by U.S. Pat. Nos. 3,283,021 (Cl. 260-666) and 3,649,704, the isomerization of normal paraffins is well known in the art. The alkylation of isoparaffins with mono-olefins is also well established as shown by U.S. Pat. Nos. 3,249,650 (Cl. 260-683.48) and 3,729,526.

The problems of isomerization catalyst deactivation caused by impurities in the feed stream is recognized in U.S. Pat. No. 3,506,733 (Cl. 260-683.68), which presents a two-step feed treatment process consisting of passage through a drying agent followed by passage through a bed of molecular sieves. In U.S. Pat. No. 3,760,029, it is disclosed that dimethylsulfide is especially harmful in butane or pentane isomerization. In U.S. Pat. No. 3,729,666 (Cl. 208-278), it is taught that the concentration of nitrogen- and sulfur-containing compounds in a refinery product stream may be reduced by emulsifying the refinery product with spent alkylation acid, mixing spent cracking catalyst with the emulsion and then separating the hydrocarbon and acid phases by settling.

Mercaptans, one form of isomerization catalyst deactivating substance, are sometimes removed by caustic extraction and catalytically promoted oxidation. This is accomplished through the use of catalysts composed of iron group metal chelates in an alkaline environment to promote the oxidation of mercaptans into disulfides which are then decanted. A suitable process is described further in U.S. Pat. Nos. 2,988,500 and 3,260,665 (Cl. 208-206).

SUMMARY OF THE INVENTION

Catalyst deactivating substances are removed from the paraffinic feed stream to an isomerization zone by contacting the feed stream with liquid hydrofluoric acid. This feed treatment step and the isomerization process are integrated with a hydrofluoric acid-catalyzed alkylation process to obtain the benefits of using a common acid regenerator and utilizing the isostripper and fluoride removal systems already present on combined isomerization-alkylation processes.

The invention may be characterized as a process for removing catalyst deactivating substances from a liquid phase hydrocarbon feed stream of a hydrocarbon conversion process which comprises the steps of: intimately contacting a liquid phase hydrocarbon feed stream with liquid hydrofluoric acid; separating the hydrocarbon feed stream from the liquid hydrofluoric acid in a settling zone; removing the hydrocarbon feed stream from the settling zone and passing the hydrocarbon feed stream into a fractionation zone in which a second process stream is fractionated; and removing the hydrocarbon feed stream from the fractionation zone and passing the hydrocarbon feed stream through a fluoride removal zone which comprises an alumina treating zone and a caustic contacting zone.

DESCRIPTION OF THE DRAWING

The drawing presents one method in which the invention may be utilized in conjunction with an integrated normal paraffin isomerization and isoparaffin alkylation process having a common fractionation zone. A feed stream to the isomerization process comprising liquid normal butane enters through line 1. It joins a stream of liquid hydrofluoric acid from line 3 and passes into line 32. The feed stream and the acid are intimately contacted in this line by passage through at least one mixing orifice 2. The resulting mixture is then passed into a separation zone comprising a settler 4 wherein the acid and hydrocarbon feed stream form two separate phases. The denser acid phase is removed from the bottom of the settler through line 5 and is mixed with a second stream of hydrofluoric acid entering through line 6 before passage into pump 7. The acid is pressurized in the pump and passed through line 8 to line 3 for recirculation through the mixing orifice and settling tank. A slip stream of the pressurized acid is removed through line 9 and passed into an acid regeneration zone 31, which is normally a purification column wherein the hydrofluoric acid is stripped from acid-soluble oils which have built up in the acid by means of a vaporous hydrocarbon such as butane.

This intimate contacting of the normal butane feed stream with the concentrated hydrofluoric acid results in the removal of substances which are detrimental to the activity of the isomerization catalyst in the reaction zone of isomerization zone 18. These substances are transferred to the acid and are removed from the process in the acid regeneration zone. The treated feed stream, which still contains some dissolved hydrofluoric acid, is removed from the settler through line 10 and passed into an isostripper 11. The isostripper functions in part as an acid removal zone to remove hydrofluoric acid and fluorides from the feed stream before it is charged to the isomerization zone. The feed stream is stripped of hydrofluoric acid in the isostripper and removed as a side-cut through line 12. The feed stream is then passed through an alumina treater 13, withdrawn through line 14 and passed into a caustic contacting zone 16. These two units remove any remaining fluorides from the feed stream. The feed stream to the isomerization process is then removed through line 17 and passed into the isomerization zone 18. The isomerization zone may contain other feed treatment steps, such as drying zones to remove water formed by the reaction of fluoride compounds with the alumina. Passage through this isomerization zone results in the production of an isomerate stream containing approximately 50% isoparaffins which is removed through line 19 and returned to the isostripper 11.

The isostripper is operated under conditions of temperature and pressure which result in the production of a vaporous mixture of isobutane, propane and hydrofluoric acid which is removed through line 20 and passed into a depropanizer 21. The lower boiling propane and hydrofluoric acid are removed as an overhead stream through line 23. This overhead stream is normally further separated to produce a liquid acid stream which is returned to the isoparaffin alkylation zone 25. Isobutane is removed from the bottom of depropanizer 21 through line 24 and passed into a hydrofluoric acid-catalyzed alkylation zone 25. In this zone, the isobutane is alkylated with a mono-olefin which enters through line 26 to form a variety of high octane branched chain paraffins referred to as alkylate. The alkylate and excess isobutane leave the alkylation zone 25 through line 27, preferably as the effluent from a settling zone, and enter the isostripper 11. Hydrofluoric acid and the excess isobutane are vaporized and removed from the isostripper through line 20, and the alkylate descends to the bottom of the isostripper 11 and is removed as the alkylation process product stream through line 28. A slip stream of the acid is removed from a settler in the alkylation zone through line 6 and passed into line 5. The acid removed from the butane treating loop in line 9 is purified in the acid-regeneration zone 31 and passed into the alkylation zone 25 via line 30. Alternative fractionation methods may be used including those in which the isoparaffins are removed from an isostripper as a sidecut.

DETAILED DESCRIPTION

The isomerization of normal paraffins is of great importance in the petrochemical and petroleum refining industries. One of the clearest indications of this is the widespread practice of isomerizing normal butane to isobutane for utilization in acid-catalyzed alkylation processes which produce high octane gasoline blending components. The optimum production capacity and return on invested capital is achieved when these processes are run on a continuous basis. It is therefore desired to maintain the activity of the isomerization catalyst at an acceptable level for as long as possible. As is known in the art, particular isomerization catalysts are adversely effected by water and by certain sulfur- or nitrogen-containing compounds which enter the process as impurities in the feed stream. It is therefore an objective of my invention to provide a process for treating the hydrocarbon feed stream of an isomerization process to remove catalyst deactivating substances. One method of removing undesired compounds is to pass the feed stream through beds of molecular sieves which selectively adsorb the undesired compounds. This method requires the regeneration of the molecular sieves or other adsorbent media used and therefore requires the switching of the feed stream and regeneration fluids between various lines and vessels. It is therefore a further objective of my invention to provide a simple and effective continuous process for the removal of undesired catalyst deactivating substances from the feed stream to an isomerization process. In particular, it is an objective of my invention to provide a method of treating the hydrocarbon feed stream to a normal paraffin isomerization process which is integrated with a hydrofluoric acid-catalyzed isoparaffin alkylation process.

The heart of an isomerization process is the passage of the feed stream through a reactor maintained at isomerization promoting conditions including the presence of an isomerization promoting catalyst. This is normally a relatively low pressure operation performed in the range of from 50 to 600 psig. and at an elevated temperature as required by the activity of the catalyst. A typical isomerization process includes the passage of hydrogen through the reaction zone to maintain vapor phase conditions and suppress coke deposition on the catalyst. The effluent from the reaction zone is normally separated into a hydrogen-rich recycle gas stream which is returned to the isomerization reactor and an isomerate-containing liquid stream which is fractionated for the production of a high purity isomerate product stream. In the integrated process shown in the drawing, the isomerate-containing liquid stream is fractionated in the isostripper. It is also a common practice to recycle an unisomerized portion of the feed stream back to the reaction. The operation of such processes is well known to those skilled in the art as is demonstrated by U.S. Pats. Nos. 2,938,936 and 3,283,021. In accordance with this teaching, the term "isomerization zone" is intended to characterize a hydrocarbon conversion zone in which a normal paraffin feed stream is passed through a reactor containing an isomerization catalyst and maintained at isomerization conditions to thereby perform a conversion of normal paraffins to isoparaffins.

The preferred isomerization promoting catalyst for use in the isomerization zone comprises a platinum group component and a halogen component supported by an inorganic oxide carrier. In general, the carrier material is a porous, high surface area material which is relatively refractory to the conditions utilized in the isomerization process. The carrier material may be selected from silica, alumina, titanium dioxide, chromium, or mixtures of these oxides; various naturally occurring refractory oxides in different degrees of purity, such as bauxite and beninite clay; or a diatomaceous earth such as kieselguhr. Of the above-mentioned oxides, alumina is preferred and particularly preferred is a synthetically prepared substantially anhydrous gamma-alumina with a high degree of purity.

The preferred platinum group component is platinum, palladium or a mixture of platinum and palladium. This however is not intended to exclude the other platinum group metals such as rhodium, ruthenium, osmium and iridium. A platinum group component may exist within the final catalytic composite as an oxide, a sulfide or a halide, etc., or as an elemental metal. On a weight basis, the platinum group component will comprise only a minor fraction of the total catalytic material. The preferred catalyst will therefore contain less than about 2.0 wt.% of the platinum group component, with the preferred concentration being from about 0.05 to about 1.0 wt.%. The method by which the platinum group component is made part of the catalytic composite is not controlling. It may therefore be added by co-precipitation or cogellation with the preferred carrier material or by ion-exchange or impregnation on pre-existing carrier material. The preferred method of preparing the catalyst impregnates the carrier material by contacting it with an aqueous solution of a water-soluble, decomposable compound of a platinum group metal. This may be performed by dipping the carrier material in a solution of chloroplatinic acid, ammonium chloroplatinate, bromoplatinic acid, or platinumdichloride. The utilization of a platinum chloride compound is preferred since it facilitates the incorporation of both the platinum component and at least a minor quantity of the halogen component in a single step.

There are also numerous ways in which to add the halogen component to the isomerization catalyst. The halogen component may be composited with the carrier material during the impregnation of the carrier material with the platinum group component by the utilization of a mixture of chloroplatinic acid and hydrogen chloride. Alternatively, the alumina hydrosol which is typically utilized to form the preferred alumina carrier material may contain at least a portion of the halogen. The halogen may also be added by contacting a calcined carrier material with an aqueous solution of an acid such as hydrogen chloride, hydrogen fluoride, or hydrogen bromide, etc. The halogen component may be selected from chlorine, fluorine, iodine, bromine or mixtures thereof with chlorine and fluorine being particularly preferred. The halogen component is normally referred to as a combined halogen and is typically present in an amount of from 0.01 to about 5.0 wt.% based on the dried support material.

A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350°C. to about 700°C. are usually satisfactory. The calcined composite is then reacted with a metal halide of the Friedel-Crafts type. Suitable metal halides include aluminum chloride, aluminum bromide, ferric chloride and zinc chloride, etc. Of these, aluminum chloride is particularly preferred.

Recently developed isomerization catalysts are of a bi-metallic or tri-metallic nature. An example of this is the catalytic composite comprising a platinum group component, a germanium component, and a Friedel-Crafts metal halide component shown in U.S. Pat. No. 3,649,704. In U.S. Pat. No. 3,652,697, there is disclosed a trimetallic catalyst comprising a platinum group component, a germanium component, a rhenium component and a Friedel-Crafts metal halide component.

In the subject process, the hydrocarbon feed stream to a normal paraffin isomerization zone, which may contain both normal and isoparaffins, is treated for the removal of substances detrimental to the activity of the isomerization catalyst by intimately contacting the liquid phase feed stream with liquid hydrofluoric acid. This intimate contacting may be performed through the use of one or more or mixing orifices such as depicted in the drawing. Alternatively, the hydrocarbon feed stream may be sprayed into a mass of liquid hydrofluoric acid. It is preferred that the hydrofluoric acid be of high purity. That is to say, the acid should be at least 80% pure by weight. The acid should also be relatively dry, and the total water content must be kept under 5% and preferably under one percent to limit the corrosiveness of the acid and thereby permit the use of low cost carbon steel in the acid handling system.

After the acid and normal paraffin feed stream are intimately contacted, they are passed into a separation zone. Due to the ease of this separation, a gravity settling tank is sufficient to effect the formation of the acid phase which is recirculated and a hydrocarbon phase which still contains some dissolved acid. The hydrocarbon residence time at the point of intimate contacting with the acid may be short since the removal of the catalyst deactivating substances is relatively instantaneous. However, a substantial residence time of from 10 to 15 minutes is desired in the gravity settler to ensure an adequate separation of the hydrocarbon phase from the acid phase. The separation zone will be operated under conditions which maintain both the acid and the normal paraffin stream as a liquid. The temperature in the settler will be determined by the temperature of incoming normal paraffin stream and the ambient temperature surrounding the settler. When the invention is utilized in conjunction with an integrated process such as depicted in the drawing, the pressure in the settling tank will be substantially the same as the pressure in the isostripper but increased slightly by the pressure drop through the connecting lines.

It is preferred to maintain a ratio of one volume of acid per volume of hydrocarbon at the point of contacting. This ratio may vary from 0.5:1 to 2:1. The feed stream contains dissolved acid after it is removed from the settler. This is removed by passing the feed stream into a fractionation unit which is operated to strip the acid from the feed stream. This acid removal zone is preferably the isostripper.

Due to the accumulation of materials formed from the catalyst deactivating substances in the hydrocarbon feed stream, such as heavy sulfur-oil complexes and polymerization products, it is necessary to pull a slip stream of the hydrofluoric acid from the hydrocarbon treating zone for regeneratin. This regeneration or purification of hydrofluoric acid by hydrocarbon removal is well known in the art. Systems for this purpose are employed for the regeneration of the hydrofluoric acid used as a catalyst in alkylation processes. An example of this is shown in U.S. Pat. NO. 3,721,720 which gives specific details of one such operation. In general, the acid to be regenerated is passed into a stripping column wherein the acid is stripped from the hydrocarbon contaminants by mens of a vaporous hydrocarbon such as butane. The term "hydrofluoric acid regeneration zone" is therefore intended to mean a distillation apparatus and related equipment which functions to separate high molecular weight hydrocarbons from the hydrofluoric acid fed to the zone by distillation and thereby produce a purified and concentrated hydrofluoric acid stream as its product. One advantage of the treating method of this invention when used in conjunction with an integrated isomerization-alkylation process is the ability to utilize the acid regeneration zone necessary for operation of the alkylation zone to regenerate the acid used to treat the normal paraffin feed stream. As shown in the drawing, acid can be withdrawn from the emulsion mixer-settler of the alkylation zone and used as the hydrofluoric acid intimately mixed with the normal paraffin feed stream. A detailed presentation of the integration of an acid regeneration zone with an alkylation process is given in U.S. Pat. No. 3,249,650. It is also known that the acid can be advantageously regenerated in the isostripper.

The invention is generally applicable to any isomerization process wherein a non-olefinic hydrocarbon feed stream contains catalyst deactivating substances which may be removed by contacting the feed stream with concentrated hydrofluoric acid. Only non-olefinic feed streams are suitable since the polymerization of an olefinic feed stream would be catalyzed by the acid. However, this is not meant to exclude the injection of olefinic material into the acid as part of a start-up procedure when it is desired to dilute fresh acid with polymeric materials. The catalyst deactivating substances removed by the acid will normally be sulfur and nitrogen containing compounds. The acid contacting step adds fluoride compounds which are also detrimental to the preferred chlorine promoted isomerization catalyst. It is therefore necessary to insert a fluoride removal zone between the fractionation zone and the isomerization zone. This fluoride removal zone will normally comprise a defluorination alumina treater and a caustic contacting means.

The invention provides a continuous method which makes it unnecessary to change the flow of the feed stream between used and regenerated adsorption zones, to regenerate these zones or replace adsorbent. The invention may be characterized as a process for isomerizing normal paraffins which comprises the steps of: intimately contacting a liquid feed stream which comprises normal paraffins with liquid hydrofluoric acid; separating the feed stream from the liquid hydrofluoric acid in a gravity settler; passing the feed stream into a hydrofluoric acid removal zone comprising a fractionation zone; passing the feed stream into a fluoride removal zone which comprises a caustic contacting zone; and, passing the feed stream into an isomerization zone containing a solid isomerization promoting catalyst and operated under conditions of temperature and pressure which promote isomerization of at least a portion of the feed stream. By this process, there is effected the removal by the hydrofluoric acid of substances in the feed stream which are detrimental to the activity of the isomerization promoting catalyst and the separation of hydrofluoric acid and fluoride compounds from the feed stream.

My invention is also specifically applicable to an integrated process for the alkylation of isoparaffins with low-boiling mono-olefins having from two to about five carbon atoms per molecule, such as ethylene, propylene. Saturated branched chain isoparaffins having from 4 to about 7 carbons atoms per molecule, such as isobutane or isopentane, are formed in the isomerization zone. The alkylation in this integrated process is promoted through the presence of concentrated liquid phase hydrofluoric acid within the alkylation reaction zone. Alkylation conditions in general include a pressure sufficient to maintain the hydrocarbons and the acid in a liquid phase, with a general pressure range being from about 20 psig. to about 500 psig., and with a more preferred range being from 100 psig. to about 250 psig. It is particularly preferred that the pressure of the alkylation zone be approximately 150 psig. and essentially "float" on the pressure maintained within the isostripper. Although the alkylation reaction may be performed at temperatures from below 0°F. to about 200°F., it is preferred to operate the commercially prevalent isoparaffin-olefin alkylation process in the range of from about 50°F. to about 120°F., with 90°F. being a representative and particularly preferred operating temperature.

Typical operating conditions in the alkylation zone also include a high molar ratio of the isoparaffinic material to the olefinic material in order to produce a high quality alkylate by encouraging monoalkylation instead of polymerization. A broad range of the ratios used is from about 6 to about 20 with a preferred operating range being from 10 to 14, and with a particularly preferred isoparaffin to olefin ratio being 12:1. A second ratio which varies in competing alkylation processes is the volume ratio of the acid to hydrocarbon in the total emulsion formed, that is, the ratio in the material charged to the mixing zone or reaction point of the alkylation process. This ratio may vary widely from a high or about 10:1 to a low of about 0.5:1, but it is preferred that the alkylation zone is operated with an acid to hydrocarbon ratio of about 1.5:1.

There are a great number of olefin-isoparaffin alkylation processes known to those skilled in the art. The great majority of these processes will operate within the range of alkylation conditions set out above. They would however have substantial differences in equipment and flow paths used in performing the alkylation. These variations are attempts to obtain optimum quality alkylate by varying the method of contacting the mono-olefin with the isoparaffin. Since this reaction occurs very rapidly, and also because hydrofluoric acid will catalyze the polymerization of the mono-olefin, the standard alkylation methods consist of either first admixing acid-free streams of olefin and isoparaffin to form a reactant mixture which is then admixed with the hydrofluoric acid, or an acid-free olefin stream is mixed with an acid-containing isoparaffin stream. In either case, a large number of ventures or mixing nozzles are normally utilized to quickly disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer settler is passed into the isostripper. This hydrocarbon phase will comprise mainly alkylate and the excess isoparaffin which was fed to the alkylation zone.

The separation of the alkylate from the excess reactants, and the separation of the iso- and normal butane streams is performed in a fractionator normally referred to as an isostripper. The design and operation of these fractionators is well known to those skilled in the art. A specific example of the operation of an isostripper is presented in the example below. Other methods of operating isostrippers are also common. The invention is not limited to the use of a single fractionator in the fractionation zone. Instead, the fractionation zone used to perform the various separations set out above may consist of two or more separate fractionating columns. This is in addition to the optional depropanizer which is shown in the drawing. In one alternative configuration, the fractionation zone may consist of two fractionating columns, with the feed stream, the alkylate containing effluent stream from the alkylation zone and the isomerization zone effluent stream all being fed to the first fractionating column. A bottoms stream comprising the alkylate formed in the alkylation zone, the normal paraffins from the feed stream and a portion of the isomerization zone effluent are then withdrawn from the first fractionating column and fed to a second fractionating column wherein the alkylate and normal paraffins are separated. The feed stream to the isomerization zone is removed as the overhead product stream of the second fractionating column.

The isomerization zone itself may contain one or more fractionating columns for the separation of the isomerization reactor effluent. For instance, this effluent may be fractionated to provide a relatively pure isomerization zone product and to allow the immediate recycle of the unisomerized normal paraffins to the isomerization reactor. A fractionating column may also be used in the isomerization zone to stabilize the effluent of the isomerization reactor, that is to remove low-boiling hydrocarbons, such as propane, before charging the effluent of the isomerization zone to the fractionation zone.

In the example given below, it is indicated that at least a portion of the isomerization zone effluent is combined with the feed stream which has passed through the hydrofluoric acid treating zone before it is injected into the fractionation zone. This is done to increase the isoparaffin content of the streams fed into the isostripper so that the optimum feed point of these streams is above the withdrawal point of the normal butane side cut. In this way, all the hydrofluoric acid-containing stream enters the isostripper above the tray at which the normal butane side cut is taken, and there are provided a sufficient number of fractionation stages to effect the removal of a substantial portion of the hydrofluoric acid from the normal paraffin phase charged thereto. The exact proportion of this mixing of the isomerization zone effluent stream with the acid treating zone effluent stream will depend on the relative ratio of isobutane and normal butane in the feed stream to the process.

In accordance with the terminology defined above, my invention may be described as a process for the hydrofluoric acid-catalyzed alkylation of isoparaffins with mono-olefins, which process comprises the steps of: intimately contacting a feed stream comprising liquid phase normal paraffins with liquid hydrofluoric acid; separating the feed stream from the liquid hydrofluoric acid in a settling zone; passing the feed stream into a fractionation zone operated under conditions which promote the removal of dissolved hydrofluoric acid from the feed stream; withdrawing the feed stream from the fractionation zone and passing the feed stream through a fluoride removal zone; passing the feed stream into an isomerization zone containing a solid isomerization catalyst and operated under conditions of temperature and pressure which promote the isomerization of the feed stream to effect the production of an isomerization zone effluent stream comprising isoparaffins; passing at least a portion of the isomerization zone effluent stream into the fractionation zone; withdrawing an isoparaffin-rich stream from the fractionation zone and passing at least a portion of the isoparaffin-rich stream into a hydrofluoric acid-catalyzed alkylation zone wherein isoparaffins contained in the isoparaffin-rich stream are reacted with mono-olefins to form an alkylate; passing the alkylate into the fractionation zone in admixture with isoparaffins; and, withdrawing a high purity alkylate stream from said fractionation zone as the product stream of the process.

EXAMPLE

This example is intended to provide a better understanding of the operation of the preferred embodiment as depicted in the drawing. In general, a normal butane stream is intimately contacted with hydrofluoric acid and then separated into a hydrofluoric acid phase and a normal butane phase containing dissolved hydrofluoric acid which is charged into the isostripper 11. A substantial portion of the hydrofluoric acid is removed by a stripping action in the isostripper and a butane-rich stream is recovered as a sidecut in line 12, treated to remove residual hydrofluoric acid and fluorides and then passed into isomerization zone 18. The isomerization zone effluent stream is returned to the isostripper and fractionated to produce an isobutane-rich stream which is removed by line 20. Propane, lighter hydrocarbons and hydrofluoric acid vapors are removed from this stream and the remaining portion is fed to the hydrofluoric acid-catalyzed alkylation zone 25. A portion of the isobutane is therein alkylated with propylene or a butylene to form an alkylate. This alkylate is removed from the settling section of the alkylation zone and passed into the isostripper. A high purity alkylate stream is recovered from the isostripper as a bottoms product and unreacted isoparaffin is recirculated to the alkylation zone.

As a specific example, a 19,808 lb./hr. stream, comprising 95.2 moles per hour of isobutane and 234.6 moles per hour of n-butane, derived from the gas concentration unit of a fluidized catalytic cracking process is fed into the overhead receiver of a distillation drying column having about thirty trays. Any water separating out as a separate phase is decanted from the overhead receiver and the remaining butanes are charged to the top of the drying column. A stream of dry butanes is removed from the bottom of the column, cooled by heat exchange and mixed with liquid hydrofluoric acid previously used in the alkylation zone to form a mixture which is about 50% butane and 50% acid. This mixture is then passed through five mixing orifices each having a 5 psig. pressure drop to provide intimate contacting. The mixture is then discharged into a horizontal gravity settler 4, and it divides into an acid phase and a hydrocarbon phase containing some hydrofluoric acid. The acid phase is decanted and recirculated with a slip stream being removed for regeneration and recycling to the alkylation zone. The settler is operated at ambient temperatures and a pressure of about 160 psig.

The butane hydrocarbon phase is removed from the gravity settler and mixed with a 28,482 lb./hr. isobutane-rich stream derived from the isomerization zone. This stream contains 276.2 moles/hr. of isobutane and 207.4 moles/hr. of normal butane. The resulting mixture is divided into two fractions which are charged to the 25th and 45th trays of the isostripper. The upper fraction is fed to the isostripper at about 175°F. and the lower fraction at 180°F. The isostripper is operated at a pressure of about 150 psig. The overhead product of the isostripper consists of about 381,951 lbs./hr. of isobutane and lighter hydrocarbons. About 5,436 lbs./hr. of propane are removed from the isostripper overhead product in the depropanizer 21. The remaining portion of the isostripper overhead is then passed into the hydrofluoric acid-catalyzed alkylation zone 25.

The alkylation zone is of the water cooled type and utilizes recirculation of the settled acid. It is designed to operate at about 95°F. with an acid to hydrocarbon volume ratio of about 1.5:1 and an isobutane to olefin mole ratio of about 12:1. The mono-olefins utilized in the alkylation zone are contained in a 35,320 lb./hr. stream derived from the gas concentration unit of a fluidized catalytic cracking process. It is composed of 220.2 moles/hr. of propylene, 227.2 moles/hr. of butenes, 120.9 moles/hr. of isobutane, 97.9 moles/hr. of propane and 33.8 moles/hr. of normal butane. The alkylate formed in this zone, the excess isobutane and the other remaining hydrocarbons are substantially separated from the acid-catalyst in a settler and returned to the isostripper at the top tray at about 150°F. This stream is about 411,782 lbs./hr., and there is in addition about 4,160 lbs./hr. of acid dissolved in the hydrocarbon stream.

The normal butane-rich charge stream to the isomerization zone is removed from the isostripper as a sidecut taken at about the 69th tray. This stream contains about 475.3 moles/hr. of normal butane, 25.0 moles/hr. of isobutane and 2.5 moles/hr. of isopentane for a combined flow of 29,258 lbs. of hydrocarbons per hour. This material is heated to a temperature of about 450°F. and passed downflow through an alumina treater at a pressure of about 105 psig. Two "swing" treaters are used to remove fluorides from this butane-rich stream. The effluent of the alumina treaters is then cooled to about 100°F. and passed downflow through a KOH contactor at about 90 psig. to ensure complete removal of all fluorides. The isomerization zone is operated under conditions which include a reactor inlet temperature of from 300°F. to 400°F. depending on the age of the catalyst and conversion desired. The isomerization reactor is operated at about 450 psig. with the LHSV through the reactor being about 4.0 and a hydrogen to hydrocarbon ratio in the reactor of about 0.5:1.0. An isomerization catalyst made in accordance with the teachings of U.S. Pat. No. 2,999,074 is utilized. About 442 lbs./hr. of make-up gas, mainly hydrogen, is fed to the isomerization zone from a reforming zone. The effluent of the isomerization zone reactor is separated to produce a bottoms stream of 28,482 lbs./hr., which, as previously mentioned, is mixed with the acid treated butane feed stream and fed to the isostripper.

The product of the process is 48,863 lbs./hr. stream of a two pound Reid vapor pressure alkylate having an average molecular weight of 106.6 and which is removed from the isostripper as a bottoms stream. Included in the product stream are 430.5 moles/hr. of $C_6$ plus alkylate 18.4 moles/hr. of isopentane, 4.7 moles/hr. of normal pentane and 4.6 moles/hr. of normal butane. About 1750 lbs./hr. of acid is removed from the alkylation zone for regeneration. The regeneration is performed by stripping the acid from about 50 lbs./hr. of tar-like impurities with 3,248 lbs./hr. of superheated isobutane charged to the regnerator at 450°F. and 160 psig. The overhead vapors of the regenerators are condensed and returned to the process.

I claim as my invention:

1. A process for the isomerization of a liquid normal paraffin feed stream containing water, sulfur and nitrogen contaminants which are detrimental to solid isomerization catalyst, which process comprises the steps of:
    a. contacting said liquid feed stream with liquid hydrofluoric acid to remove aforesaid detrimental contaminants therefrom;
    b. separating the treated feed stream of step (a) from contaminant-containing liquid hydrofluoric acid;
    c. stripping the treated feed stream of step (b) in a fractionation zone to remove hydrogen fluoride therefrom;
    d. treating the stripped feed stream of step (c) for the removal of any remaining fluorides therefrom;
    e. contacting the thus purified feed stream of step (d) with solid isomerization catalyst at isomerization conditions;
    f. introducing the isomerization effluent of step (e) to said fractionation zone of step (c) for fractionation therein together with said treated feed stream; and
    g. withdrawing isoparaffin product from said fractionation zone.

2. The process of claim 1 further characterized in that the fluoride removal in step (d) is effected by successive contact of said stripped feed stream with alumina and caustic.

3. The process of claim 1 further characterized in that the feed stream and the liquid hydrofluoric acid are intimately contacted by their simultaneous passage through a mixing orifice.

4. The process of claim 1 further characterized in that the feed stream and the liquid hydrofluoric acid are intimately contacted by spraying a fine dispersion of the feed stream into a quantity of the acid.

5. A process for the isomerization and subsequent alkylation of a liquid normal paraffin feed stream containing water, sulfur and nitrogen contaminants which are detrimental to solid isomerization catalyst, which process comprises the steps of:
    a. contacting said liquid feed stream with liquid hydrofluoric acid to remove aforesaid detrimental contaminants therefrom;
    b. separating the treated feed stream of step (a) from contaminant-containing liquid hydrofluoric acid;
    c. stripping the treated feed stream of step (b) in a fractionation zone to remove hydrogen fluoride therefrom;
    d. treating the stripped feed stream of step (c) for the removal of any remaining fluorides therefrom;
    e. contacting the thus purified feed stream of step (d) with solid isomerization catalyst at isomerization conditions;
    f. introducing the isomerization effluent of step (e) to said fractionation zone of step (e) for fractionation therein together with said treated feed stream;
    g. stripping isoparaffin from said fractionation zone and reacting the same with mono-olefin in contact with hydrofluoric acid catalyst at alkylation conditions;
    h. supplying resultant hydrocarbon phase separated from step (g) containing alkylate in admixture with unreacted isoparaffin to said fractionation zone; and
    i. removing a high purity alkylate product from the lower portion of said fractionation zone.

6. The process of claim 5 further characterized in that said fractionation zone comprises an isostripper used in a process for the hydrofluoric acid-catalyzed alkylation of isoparaffins.

7. The process of claim 5, further characterized in that the feed stream to step (a) comprises normal paraffins having from 4 to 7 carbon atoms per molecule.

8. The process of claim 7 further characterized in that the mono-olefin contains from 2 to 5 carbon atoms per molecule.

9. The process of claim 5 further characterized in that hydrofluoric acid which has been contacted with the feed stream in step (a) hydrofluoric acid which has been used as catalyst in the alkylation of step (g) are regenerated and the regenerated acid is recycled to the alkylation of step (g).

10. The process of claim 8 further characterized in that hydrofluoric acid withdrawn from the alkylation of step (g) is used as the hydrofluoric acid contacted with the feed stream in step (a).

11. The process of claim 5 further characterized in that hydrofluoric acid catalyst is supplied from alkylation step (g) to step (a).

12. The process of claim 8 further characterized in that at least a portion of the isomerization effluent of step (a) is combined with the feed stream of step (b) prior to passage of said feed stream into the fractionation zone in step (c).

* * * * *